(12) United States Patent
Levatter

(10) Patent No.: US 7,848,378 B2
(45) Date of Patent: Dec. 7, 2010

(54) APPARATUS AND METHOD FOR MONITORING POWER OF A UV LASER

(75) Inventor: Jeffrey I. Levatter, Solana Beach, CA (US)

(73) Assignee: Photomedex, Inc., Montgomeryville, PA (US)

( * ) Notice: Subject to any disclaimer, the term of this patent is extended or adjusted under 35 U.S.C. 154(b) by 0 days.

(21) Appl. No.: 11/498,382

(22) Filed: Aug. 3, 2006

(65) Prior Publication Data
US 2007/0030877 A1    Feb. 8, 2007

Related U.S. Application Data

(60) Provisional application No. 60/705,789, filed on Aug. 5, 2005.

(51) Int. Cl.
*H01S 3/22* (2006.01)
(52) U.S. Cl. .......................... 372/57; 372/61
(58) Field of Classification Search ............ 372/32, 372/57, 61, 103, 59
See application file for complete search history.

(56) References Cited

U.S. PATENT DOCUMENTS

| | | | |
|---|---|---|---|
| 3,404,349 A | 10/1968 | Rigrod | |
| 3,437,955 A | 4/1969 | Enloe et al. | |
| 3,471,803 A | 10/1969 | Forster | |
| 3,572,948 A | 3/1971 | Catherin | |
| 3,596,201 A | 7/1971 | Chester | |
| 3,831,108 A | 8/1974 | Le Floch | |
| 4,891,818 A * | 1/1990 | Levatter | 372/57 |
| 5,463,650 A * | 10/1995 | Ito et al. | 372/57 |
| 5,642,374 A * | 6/1997 | Wakabayashi et al. | 372/57 |
| 5,657,334 A * | 8/1997 | Das et al. | 372/33 |
| 6,018,535 A * | 1/2000 | Maeda | 372/20 |
| 6,272,158 B1 * | 8/2001 | Kleinschmidt et al. | 372/32 |
| 6,526,071 B1 * | 2/2003 | Zorabedian et al. | 372/20 |
| 6,608,848 B2 * | 8/2003 | Kleinschmidt et al. | 372/32 |
| 6,661,815 B1 * | 12/2003 | Kozlovsky et al. | 372/20 |
| 6,721,344 B2 * | 4/2004 | Nakao et al. | 372/55 |
| 6,724,797 B2 * | 4/2004 | Daiber | 372/92 |
| 6,741,627 B2 * | 5/2004 | Kitatochi et al. | 372/57 |
| 2002/0126717 A1 * | 9/2002 | Nasu et al. | 372/32 |
| 2003/0161374 A1 * | 8/2003 | Lokai | 372/57 |
| 2005/0015124 A1 | 1/2005 | Irwin | |
| 2005/0175055 A1 * | 8/2005 | Levatter | 372/57 |

* cited by examiner

*Primary Examiner*—Minsun Harvery
*Assistant Examiner*—Tuan N. Nguyen
(74) *Attorney, Agent, or Firm*—Knobbe, Martens, Olson & Bear, LLP

(57) ABSTRACT

An excimer laser includes a chamber for containing laser gas, electrodes in the chamber disposed to excite the laser gas, thereby producing optical emissions, first and second mirrors arranged to form a resonator cavity, and a detector disposed to receive a portion of light transmitted through the first mirror. The first mirror is more reflective than the second mirror.

16 Claims, 2 Drawing Sheets

APPARATUS AND METHOD FOR MONITORING POWER OF A UV LASER

CROSS-REFERENCE TO RELATED APPLICATIONS

This application claims priority under 35 U.S.C. §119(e) to U.S. Provisional Application Ser. No. 60/705,789, filed Aug. 5, 2005, entitled "Power Monitor for UV Laser," which is incorporated herein by reference in its entirety.

BACKGROUND

1. Field

The present invention relates to rare gas-halogen excimer lasers and, in particular, to increasing the operational lifetime, reliability, efficiency, and/or performance of such lasers.

2. Description of the Related Art

An excimer laser uses a rare gas such as krypton (Kr), xenon (Xe), argon (Ar), or neon (Ne), and a halide gas or a gas containing a halide, for example fluorine ($F_2$) or hydrogen chloride (HCl), as the active components. The active components, and possibly other gases, are contained in a pressure vessel provided with longitudinally extending lasing electrodes for inducing a transverse electrical discharge in the gases. The discharge causes the formation of excited rare gas-halide molecules whose disassociation results in the emission of ultraviolet photons constituting the laser light. Many excimer lasers use xenon chloride (XeCl) as the medium for generating light at a specific wavelength (e.g., at about 308 nanometers (nm)). The laser further comprises mirrors or reflective surfaces that form an optical cavity to establish an optical resonance condition. Such a system is also described in U.S. patent application Ser. No. 10/776,463, filed Feb. 11, 2004, entitled "Rare Gas-Halogen Excimer Laser with Baffles," which is incorporated herein by reference in its entirety. The chamber may include inlet and outlet ports for flow of gases into and out of the chamber.

Such lasers may optionally include a feedback system wherein a fraction of the light in the output laser beam is extracted to monitor the performance of the laser. What is needed are efficient and effective feedback systems for excimer lasers.

SUMMARY

In certain embodiments, an excimer laser comprises a chamber for containing laser gas, electrodes in the chamber disposed to excite the laser gas, thereby producing optical emissions, first and second mirrors arranged to form a resonator cavity, and a detector disposed to receive a portion of light transmitted through the first mirror. The first mirror is more reflective than the second mirror.

In certain embodiments, an excimer laser comprises a means for containing laser gas, a means for exciting the laser gas, thereby producing optical emissions, first and second means for reflecting the optical emission, and a means for detecting light transmitted through the first reflecting means. The first and second reflecting means are arranged to produce optical resonance. The first reflecting means is more reflective than the second reflecting means.

DETAILED DESCRIPTION OF THE PREFERRED EMBODIMENTS

Excimer lasers can emit pulses of ultraviolet radiation and have potentially many practical applications in medicine, industry, and communications.

Ultraviolet light, for example emitted by an excimer laser, may be employed to treat a variety of skin disorders such as, for example, psoriasis and vitiligo. Exemplary systems and methods for providing such treatment are described in U.S. patent application Ser. No. 10/799,337, filed Feb. 27, 2002, entitled "Treatment of Skin Disorders with UV Light and Cooling," which is incorporated herein by reference in its entirety. Such systems may include an ultraviolet light source, such as a laser (e.g., excimer laser), and a delivery system (e.g., a handpiece).

The laser energy can be coupled from the laser chamber and delivered to a treatment site (e.g., on a patient) by using a flexible or rigid optical line, such as a fiberoptic cable or liquid light guide. The laser energy can also be delivered by using a delivery system including one or more mirrors. The light output by the excimer laser may be guided or may propagate in free space such as through the air to a target, e.g., for treatment. A wide variety of systems are possible.

As described herein, an excimer laser is a type of gas laser wherein gases are used to generate ultraviolet light. The gas fills an open space between a pair of bulk optic reflectors, e.g., mirrors, arranged to form an optically resonant cavity. De-excitation of gaseous molecules provides light that propagates in waves in free space (as opposed to waveguides) between the mirrors. This light reflects back and forth within the gas-filled open space between the mirrors. The laser gas introduces gain to the light propagating in the resonator cavity producing lasing. A portion of the laser light passes through one of the mirrors thereby providing a laser beam that can be used for applications such as described above.

Figure 1:
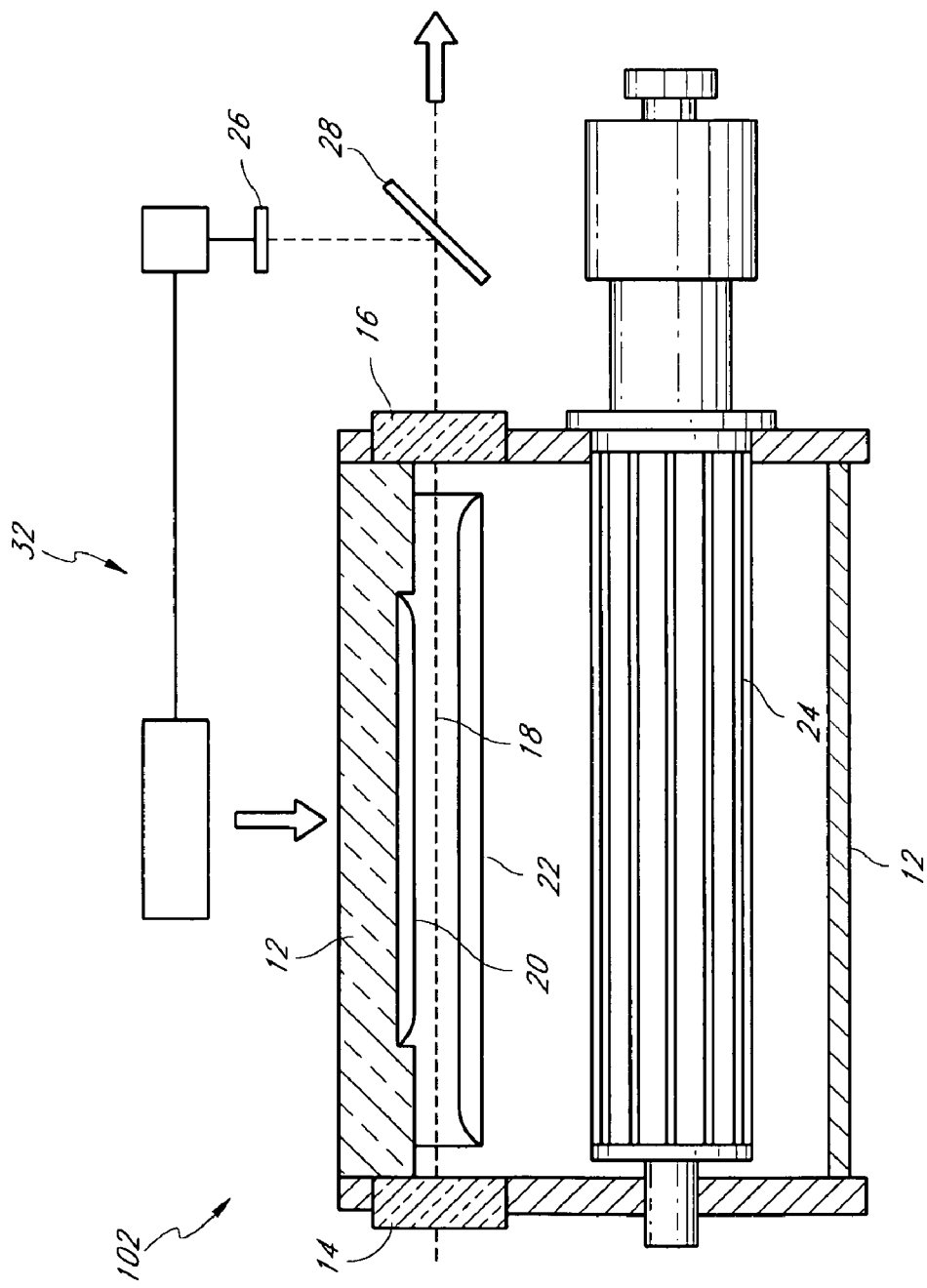
FIG. 1 is a schematic, lengthwise cross-sectional view of an embodiment of an excimer laser having a feedback system for adjusting the laser based on measurements of light extracted from the output laser beam.

FIG. 1 illustrates a cross-sectional view of an example laser 102. The laser 102 comprises a chamber 12 for containing laser gases. Lasing electrodes 20, 22 longitudinally extending within the chamber 12 are configured to induce a transverse electrical discharge in laser gases within the chamber 12. The electrical discharge causes the formation of excited rare gas-halide molecules, whose disassociation results in the emission of ultraviolet photons constituting the laser light. The laser further comprises reflective optical elements 14, 16 (e.g., near totally reflective mirrors, partially reflective mirrors, etc.) that form an optical cavity to establish an optical resonance condition. Laser gases within the chamber 12 can be circulated in the space between the lasing electrodes 20, 22 by a fan 24. The laser gases may be cooled by a heat exchanger, i.e., a structure that removes excess heat, and the like.

As described above, laser energy is generated within the chamber 12 and, more particularly, in the resonator cavity formed by the first and second mirrors 14, 16. In the embodiment shown in FIG. 1, first and second mirrors 14, 16 are disposed at two opposing internal faces of the chamber 12. In various embodiments, these mirrors may comprise bulk mirrors comprising, for example, glass, sapphire, fused silica, or other substrates optically transmissive to the laser light. This transmissive substrate has a reflective coating thereon that is reflective to the laser light. For excimer lasers that output UV light, for example, such substrates may transmit UV light while the reflective coatings may reflect UV light. Other designs are possible.

In certain embodiments, for example, the first mirror 14 is designed to have a nearly 100% reflectance, though in fact there will ineluctably be some modicum of laser energy that is transmitted through the first mirror 14. The mirror may, for example, have a reflectance at the laser wavelength (e.g., 308 nm) of greater than about 99.0% and greater than about 99.9% in some embodiments. The second mirror 16 is designed to be partially reflecting. The second mirror 16 may, for example, allow about 50% of the laser energy striking it to pass through the mirror, and may reflect about 50% back to the other mirror. In other embodiments, the second mirror 16 transmits between about 1% and 90% of the laser energy and reflects between about 99% and 10% of the laser energy. Accordingly, in various embodiments, the first mirror 14 is more reflective and may be substantially more reflective than the second mirror 16. In some embodiments, the second mirror 16 is more transmissive and may be substantially more transmissive than the first mirror 14.

The energy delivered by the laser 102 may fluctuate. In order to monitor the extent of such fluctuation, a detector 26 (e.g., a photodiode) may be disposed so as to receive light transmitted through the second mirror 16. A partially reflecting surface or mirror 28 (e.g., a beam splitter) may be disposed in the optical path 18 of the energy transmitted through the second mirror 16. The beam splitter 28 may shunt, for example, between about 1% and 5% of the light transmitted through the second mirror 16 into the detector 26.

Figure 2:
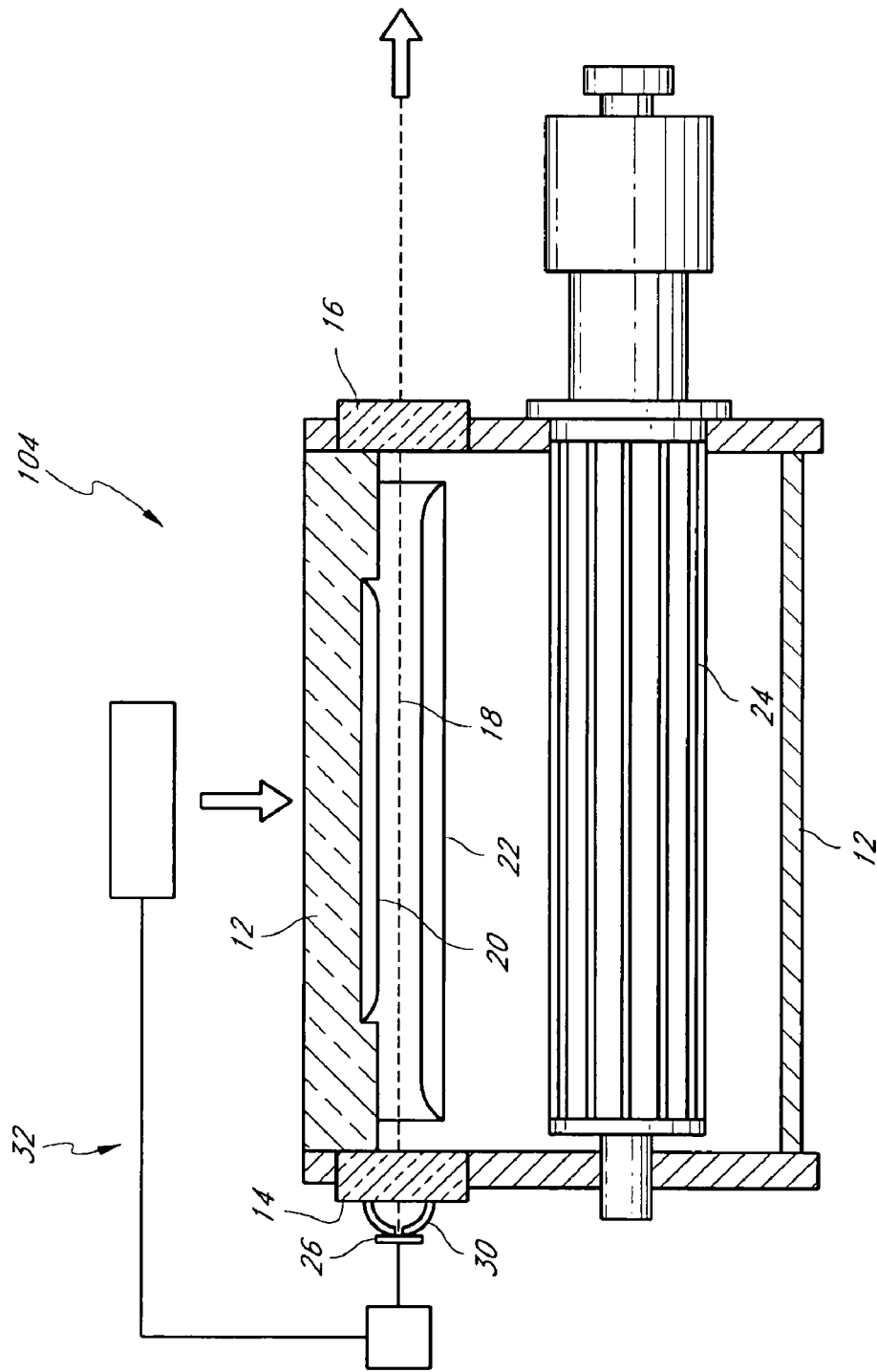
FIG. 2 is a schematic, lengthwise cross-sectional view of another embodiment of an excimer laser with an alternative feedback arrangement.

FIG. 2 illustrates another embodiment of a laser 104 including a first mirror 14 and a second mirror 16. An optical detector 26 (e.g., a photodiode) is disposed to receive a portion of the light transmitted through the first mirror 14. For example, the detector 26 may be placed proximate to the first mirror 14. In certain embodiments, an optical integrating sphere 30 or collecting optics or can be positioned to capture the energy that manages to pass through, or "leak from," the first mirror 14. These collecting optics may comprise bulk optics in the form of a lens or a reflecting surface such as a reflecting mirror. One example of collection optics comprising a reflecting surface is an integrating sphere. The integrating sphere 30 can capture the leaked optical energy, and then output a portion of the light to the detector 26. The integrating sphere 30 may also homogenize the beam output through the first mirror 14.

The term integrating sphere 30 is used to describe the reflective collecting optic used to collect light that passes through the first mirror 14, even though the reflective optic is more akin to a hemisphere. The reflecting optic therefore may be a spherical surface that is more or less than a hemisphere. In other embodiments, the reflective surface need not be spherical in shape. Spheres, facets, or other reflective structures are possible. This reflecting surface may be disposed, e.g., opposite to the first mirror 14, enclosing or covering a portion of the first mirror 14, etc., so as to receive light passing through the first mirror 14. In various embodiments, however, light transmitted through the first mirror 14 reflects from the reflective surface back toward the first mirror 14. This light may be reflected from the first mirror 14 to the detector 26 or may reflect multiple times between the reflective surface and the first mirror 14 until the light is incident on the detector. In this fashion, however, the reflective surface may increase the amount of light transmitted through the first mirror 14 that is received by the detector. Because only a small amount of light may be transmitted by the first mirror 14, increasing the collection efficiency of the detector 26 is advantageous.

In certain preferred embodiments, the detector 26 is linked to, and in communication with, a feedback/control system ("controller") 32 that is configured to increase or decrease laser energy output, for example depending on whether a fluctuation falls outside a band of acceptable output. The detector 26 and the controller 32 may be calibrated, for example by analyzing a relationship between a known quantity of energy and an amount of energy received by the detector 26. The relationship may then be used to determine how much energy is output from the laser 104 for various amount of energy received by the detector 26. For example, if the calibration shows that the detector 26 receives about 0.5% of the energy emitted by the laser 104, and the detector measures 50 milliwatts (mW), then the laser 104 is producing about 1 watt (W) of power.

In some embodiments, the controller 32 is configured to adjust the energy or power output from the laser 104 if the detected energy output differs from a target energy output. For example, if a medical procedure preferably utilizes a power of 1 W, that power would be the target power output for the laser 104. Over a certain period of time (e.g., the time to complete a treatment procedure), the controller 32 may be programmed to adjust conditions of the laser 104 (e.g., input voltage, gas pressure, temperature) in order to compensate for fluctuations in output power or energy. For example, the controller 32 may be configured to stabilize the output energy to within about 20%, 10%, 5%, or less of a mean power or energy for the duration of a treatment of a patient. Other methods of calibration are also possible.

An example benefit of the configuration shown in FIG. 2 is that instead of using, and losing, for example, between about 1% and 5% of the energy from the otherwise useable output from the laser 102 that passes through the second mirror 16, the otherwise unavoidable and unusable loss from the first mirror 14 is utilized by the laser 104. Because the portion of the beam used, for example, for a medical procedure, is not passed through a beam splitter 28 such as shown in FIG. 1, the useable output from the laser, for example, that can be delivered to a patient may be increased. Embodiments such as those depicted in FIG. 2 may suitably be referred to as a "zero loss" laser energy detecting device, as none of the usable laser power/energy is lost due to the detector.

An additional benefit to disposing the detector 26 so as to receive a portion of the light from the more reflective first mirror 14, rather than downstream of a reflective surface of a beam splitter 28, is that system cost can be reduced. In embodiments including an integrating sphere 30, an integrating sphere 30 typically costs less than a beam splitter 28 (e.g., costing about 25% as much). Moreover, in some embodiments, the integrating sphere 30 reduces or eliminates measurement errors due to laser beam power density inhomogeneities. Some embodiments may omit the integrating sphere, thereby having a cost similar to a laser without a beam splitter 28.

A wide variety of variations are possible. Components may be added, removed, or reordered. Different components may be substituted out. The arrangement and configuration may be different. Similarly, processing steps may be added or removed, or reordered.

While the foregoing detailed description discloses several embodiments of the present invention, it should be understood that this disclosure is illustrative only and is not limiting of the present invention. It should be appreciated that the specific configurations and operations disclosed can differ from those described above, and that the methods described herein can be used in other contexts.

What is claimed is:

1. An excimer laser outputting optical energy comprising:
a chamber for containing laser gas;
electrodes in said chamber disposed to excite said laser gas, thereby producing optical emissions;
first and second mirrors arranged to form a resonator cavity, the first mirror being more reflective than the second mirror;
a detector disposed to receive a portion of light generated within the resonator cavity and transmitted through the first mirror;
a controller in communication with the detector, the controller configured to increase the optical energy output by the excimer laser when the detector detects that the received portion of light is lower than a threshold; and
bulk collecting optics disposed between the first mirror and the detector, wherein the bulk collecting optics comprise reflecting optics disposed between the first mirror and the detector, wherein the reflecting optics comprise an integrating sphere.

2. The laser of claim 1, wherein the controller is configured to adjust the laser to provide substantially constant energy output from the second mirror.

3. The laser of claim 1, wherein the controller stabilizes the energy output through the second mirror to within about 20% of a mean energy output over a duration of treatment of a patient with the laser.

4. The laser of claim 1, wherein the controller stabilizes the energy output through the second mirror to within about 10% of a mean energy output over duration of treatment of a patient with the laser.

5. The laser of claim 1, wherein the controller stabilizes the energy output through the second mirror to within about 5% of a mean energy output over a duration of treatment of a patient with the laser.

6. The laser of claim 1, wherein the first mirror is greater than about 99.0% reflective.

7. The laser of claim 1, wherein the first mirror is greater than about 99.9% reflective.

8. The laser of claim 1, wherein the detector is disposed to measure an output of a laser beam produced by said laser without reducing energy of a usable portion of the laser beam.

9. The excimer laser of claim 1, wherein the detector comprises a photodiode.

10. The excimer laser of claim 1, wherein the controller is configured to increase the energy output of the laser at least in part by adjusting an input voltage.

11. The excimer laser of claim 1, wherein the controller is configured to increase the energy output of the laser at least in part by adjusting a gas pressure.

12. The excimer laser of claim 1, wherein the controller is configured to increase the energy output of the laser at least in part by adjusting a temperature.

13. An excimer laser outputting optical energy comprising:
a means for containing laser gas;
a means for exciting said laser gas, thereby producing optical emissions;
first and second means for reflecting said optical emission, said first and second reflecting means arranged to produce optical resonance within the containing means, the first reflecting means being more reflective than the second reflecting means, wherein the first and second reflecting means comprise bulk mirrors;
a means for detecting light generated within the containing means and transmitted through the first reflecting means, wherein the means for detecting light comprises an optical detector; and
a means for increasing the optical energy output of the excimer laser when the means for detecting light detects a low power condition.

14. The laser of claim 13, wherein the gas containing means comprises a chamber.

15. The laser of claim 13, wherein the gas exciting means comprises electrodes.

16. An excimer laser outputting optical energy comprising:
a chamber configured to contain laser gas;
electrodes in said chamber and configured to excite laser gas;
a resonator cavity in said chamber formed by a first mirror and a second mirror;
a detector configured to receive a portion of light generated within the resonator cavity and to provide a measure of the output energy of said generated light without reducing energy of a usable portion of the generated light;
an integrating sphere between the resonator cavity and the detector, wherein said first mirror is more reflective than said second mirror and wherein said integrating sphere is disposed between said first mirror and said detector; and
a controller configured to increase the output energy of the generated light when the measured output energy decreases wherein the controller is configured to adjust the laser to provide substantially constant energy output.

* * * * *